(12) United States Patent
McEllen

(10) Patent No.: US 7,763,212 B2
(45) Date of Patent: Jul. 27, 2010

(54) CEILING LIGHTING FIXTURE WITH UV-C AIR STERILIZATION

(76) Inventor: John J. McEllen, 17293 Bittersweet Trail, Chagrin Falls, OH (US) 44023

(*) Notice: Subject to any disclaimer, the term of this patent is extended or adjusted under 35 U.S.C. 154(b) by 0 days.

(21) Appl. No.: 12/512,647

(22) Filed: Jul. 30, 2009

(65) Prior Publication Data
US 2010/0003165 A1 Jan. 7, 2010

Related U.S. Application Data

(63) Continuation of application No. 11/823,507, filed on Jun. 28, 2007, now abandoned.

(51) Int. Cl.
*A61L 9/20* (2006.01)
(52) U.S. Cl. ....................................... 422/121
(58) Field of Classification Search ........................ None
See application file for complete search history.

(56) References Cited

U.S. PATENT DOCUMENTS

| | | | |
|---|---|---|---|
| 2,398,627 A | 4/1946 | Disbro et al. | |
| 3,846,072 A | * 11/1974 | Patterson | 96/222 |
| 6,497,840 B1 | 12/2002 | Palestro et al. | |
| 6,855,295 B2 | 2/2005 | Kulp | |
| 6,884,399 B2 | 4/2005 | Reisfeld et al. | |
| 6,911,657 B2 | 6/2005 | Waluszko | |
| 2004/0047776 A1 | 3/2004 | Thomsen | |
| 2004/0175288 A1 | 9/2004 | Horton, III | |
| 2005/0058584 A1 | 3/2005 | Shyu | |
| 2005/0150386 A1 | 7/2005 | Cheng | |

OTHER PUBLICATIONS

Office Action Mailed May 25, 2010, in U.S. Appl. No. 11/935,950.

* cited by examiner

*Primary Examiner*—Elizabeth L McKane
(74) *Attorney, Agent, or Firm*—Kenyon & Kenyon LLP

(57) ABSTRACT

An UV-C air sterilizer with an optional visible light provides effective air sterilization through the use of a relatively low intensity UV-C radiation field external of the fixture and the continuous circulation of a mixture of treated and untreated air. Methods are also disclosed.

22 Claims, 3 Drawing Sheets

CEILING LIGHTING FIXTURE WITH UV-C AIR STERILIZATION

This is a continuation of application Ser. No. 11/823,507 filed 28 Jun. 2007, now abandoned, the content of which is incorporated herein by reference.

BACKGROUND OF THE INVENTION

The present invention relates to an efficient room lighting fixture with safe and effective air sterilization, and finds particular application in public spaces such as hospitals, health care institutions, dormitories, schools and offices.

Short wave ultra violet (UV-C) energy has long been used for air sterilization. The usefulness of UV-C irradiation on air quality lies in the effect on germs (microorganisms) transmitted in aerosolized form. Such infectious germs are generally less than 0.3 microns in diameter and are suspended or "float" in the air.

Different types of microorganisms vary significantly in their resistance to W-C irradiation. For example, spores such as anthrax have a "cell wall" (like bacteria) as well as an outer "shell" which must be penetrated by the W-C energy. Viruses such as influenza, the common cold, SARS, measles and small pox do not have a cell wall and are about five times more susceptible to W-C radiation than spores. Bacteria with a cell wall such as tuberculosis, even extended drug resistant (XDR) TB, may be ten times more vulnerable to W-C radiation than anthrax spores. The W-C "dose" needed to destroy germs is generally expressed as joules (one W-C watt of energy for one second) per square meter; or the equivalent $\mu J/cm^2$—micro-joules per square centimeter.

It is desirable to effect air sterilization within the room where the germs originate. However, there are safety issues. Keratoconjunctivitis (external idammation of the eye) and erythmea (reddening of the skin) can result from overexposure to W-C and the National Institutes for Occupational Safety and Health (NIOSH) recommends an upper limit on the amount of W-C radiation for the safety of personnel in the room, i.e., 6 $\mu J/cm^2$—6 micro-joules per square centimeter over a continuous eight-hour period. Although they may be modified from time to time, the NIOSH guidelines must be considered in the design of fixtures for public spaces.

Because of safety considerations, air sterilization products (e.g., in-duct, ceiling and floor mounted fixtures) generally avoid UV-C radiation into a room and have attempted to confine UV-C radiation to the interior of a closed (i.e., UV-C baffled) chamber, and pass air through the baffled chamber for sterilization.

A significant factor in avoiding excessive UV-C radiation in the lower part of a room, i.e. the part of the room populated by people, is the height at which the UV-C device is located. For example, unbaffled floor and table mounted devices would emit direct UV-C radiation into the lower part of the room. Energy cost considerations have reduced ceiling heights, typically to eight feet, which exacerbates the dilemma of achieving an effective UV-C dose in the upper part of the room without exceeding acceptable limits in the lower part of the room.

Initial efforts to use wall and ceiling pendant UV-C fixtures transmitted an intense UV-C beam at a room height well above the "eye level" of people occupying the room, i.e., generally considered to be approximately 60 inches above the floor. Germ reduction occurred in the air. passing through the beam as a result of convection currents and ventilation systems. While the intensity of the beam was effective in sterilizing the air passing through the beam, the volume and velocity of the air passing through the beam was not controlled and, being thus subject to external forces, such devices have generally been ineffective. In addition, the narrowing of the beam vertically, typically through the use of louvers, wasted most of the UV-C energy making such fixtures highly inefficient.

In an attempt to address this lack of efficacy, Melvin First, Sc. D. of The Harvard School of Public Health has suggested the utilization of a ceiling mounted fan with air intake apertures at the lower end thereof and horizontal air exhaust apertures adjacent the ceiling. As illustrated in FIG. 1 (Prior Art), such a device includes an electric motor 10 with a large impeller 12. As contemplated by Dr. First, air from the room would be drawn upwardly past the motor 10 and a luminaire 14 and laterally exhausted adjacent the ceiling 15. A circular array of unspecified UV-C emitting bulbs 16, stacked three deep was to provide a high intensity UV-C source. This array was to be located circumferentially around the impeller 12 so that air laterally exhausted from the impeller 12 passed by the bulbs 16. Shielding of the lower part of the room from direct irradiation by the UV-C array was to be provided by a laterally extending baffle 18 with the entire structure supported by a number of rods 20.

The device proposed by Dr. First proved impractical for ceilings below about twelve feet because of the large size, i.e., it descended too far vertically into the room (about 24-30") and the illuminator source would be at eye level for the typical eight foot ceiling. The proposed fixture also laterally occupied too much of the ceiling (about 30-36" wide) due to the need to laterally extend the baffle limiting the angle of direct radiation into the lower part of the room.

In addition, the use of multiple UV-C sources with a single vertical opening created a steep angle of incidence of the UV-C radiation on the ceiling which would have caused significant UV-C radiation to be reflected downwardly into the lower part of the room resulting in an unacceptable radiation level.

Other disadvantages include the difficulty in accessing and replacing the UV-C lamps because of the large diameter baffle and rod suspension system. Moreover, the placement of the illumination source at the center of the air intake added to the size of the fixture and would have impeded air flow into the air mover, resulting in noise and/or motor inefficiency. Notwithstanding these deficiencies, the amount of air circulated through the device would have represented an improvement over high intensity, densely louvered, narrow beam systems relying on convection currents and room ventilation systems for air mixing.

It is an object of this invention to address the deficiencies of known room air sterilizers and to provide a novel air sterilization and lighting fixture and method. More particularly, it is an object of this invention to provide a novel lighting fixture and method that is effective in providing efficient room lighting as well as safe and effective room air sterilization.

In one aspect, the fixture of present invention uses a novel relatively low intensity and broader UV-C radiation field effective because of the increased time air remains in the field as it is circulated in the room. Because the radiation field is broader, air velocity may be decreased to reduce the noise of the air being moved and drafts to make the fixture acceptable in environments such as hospitals, public libraries, etc.

In another aspect, the compact size of the fixture of the present invention makes it acceptable for use in rooms with relatively low ceilings.

In yet another aspect, the fixture of the present invention limits the visible light emanating from the UV-C source so as to make the fixture acceptable in environments such as hospitals where it is important that the air sterilization avoid interference with the sleep of patients.

In yet another aspect, the fixture of the present invention is easily adjusted to provide a radiation field appropriate for various ceiling heights.

In a further aspect, the fixture of the present invention provides room illumination without interfering with air flow.

In yet a further aspect, the UV-C source of the present invention is readily accessible for replacement.

In still yet a further aspect, the fixture of the present invention provides remote control of the operation of the fixture and protection of all electrical and electronic components from UV-C radiation.

Many other objects and advantages will be apparent from the following detailed description of preferred embodiments when read in conjunction with the appended drawings.

THE DRAWINGS

THE WRITTEN DESCRIPTION

Figure 1:
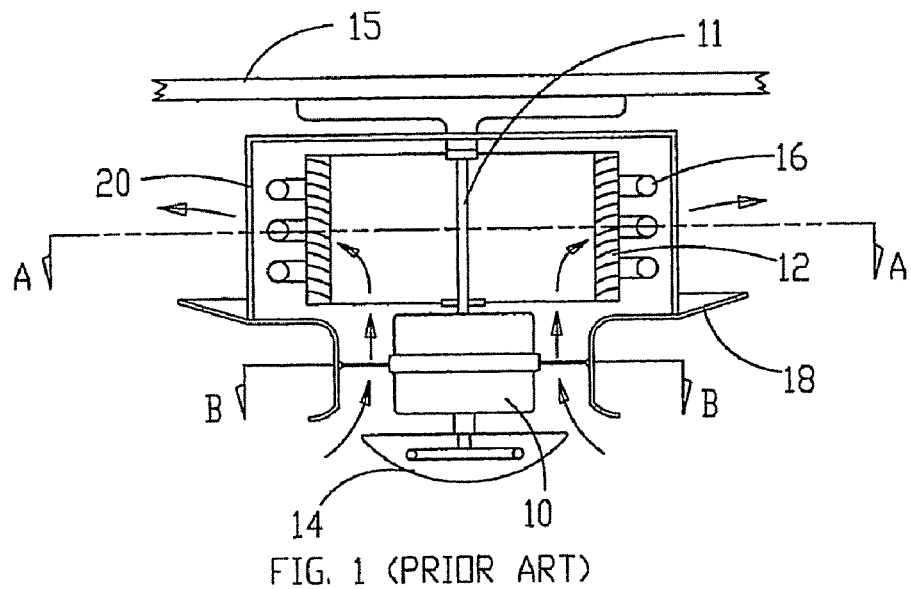
FIG. 1 (prior art) is a concept drawing illustrating the proposed fixture of Dr. First.
Figure 1A:
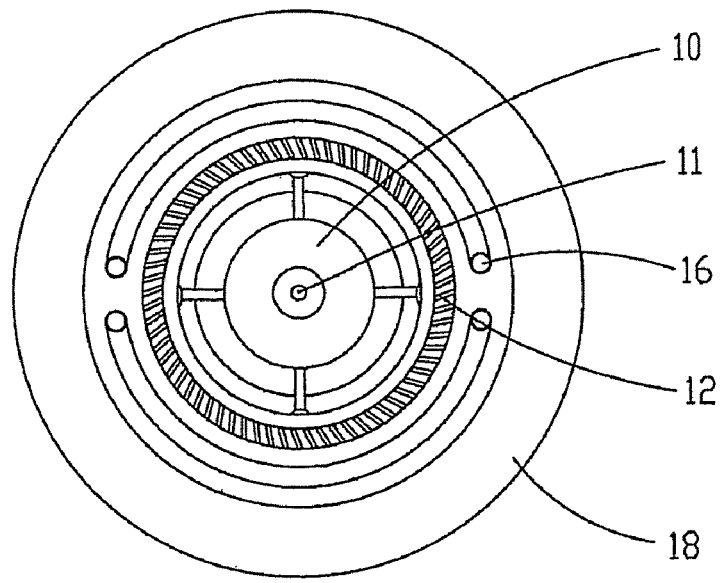
FIGS. 1A and 1B (prior art) are sections taken through lines A-A and B-B respectively of the concept drawing of FIG. 1.
Figure 1B:
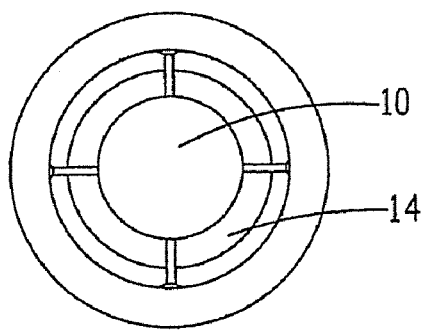
Figure 2:
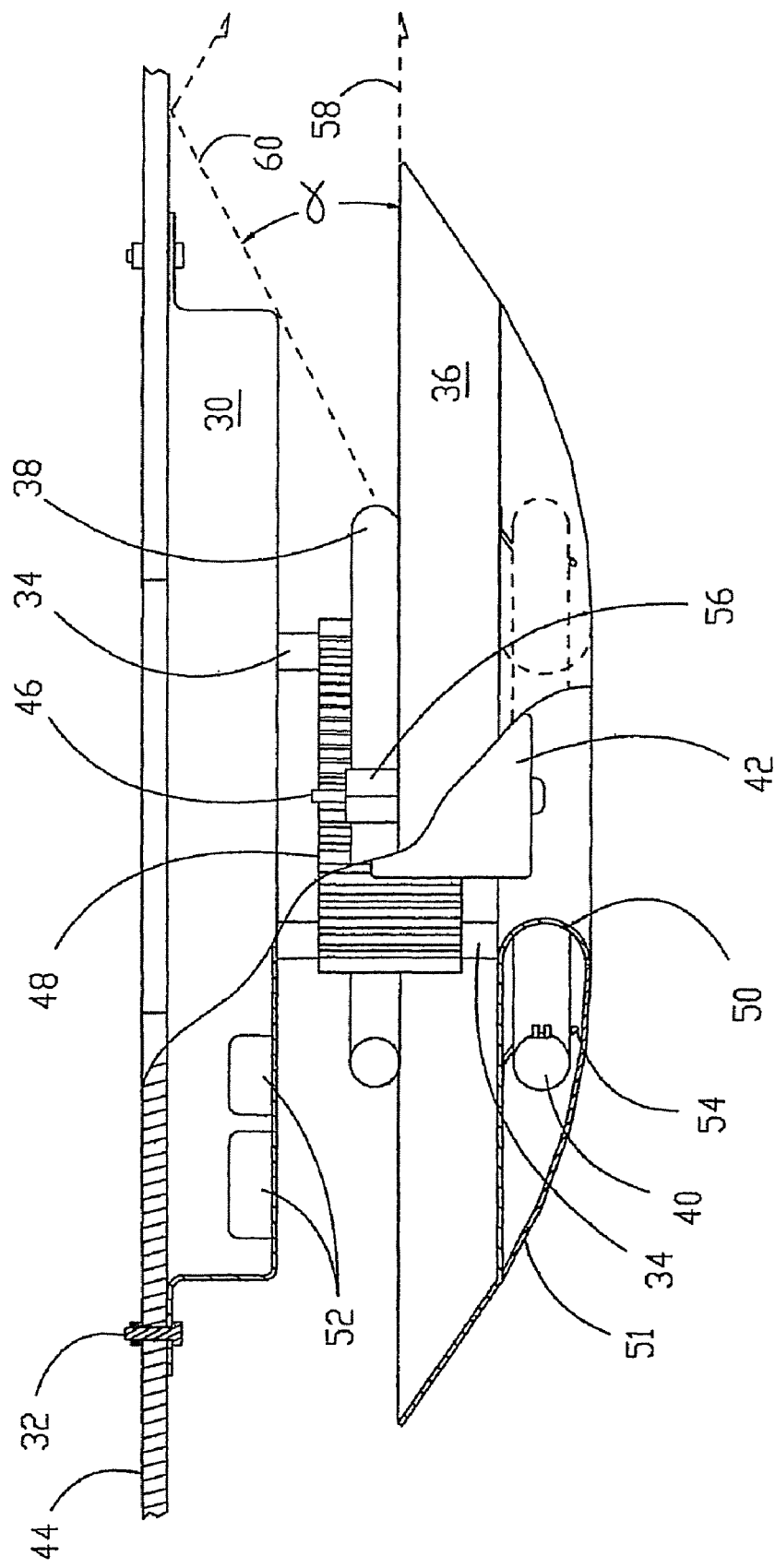
FIG. 2 is an elevation in partial section of one embodiment of the fixture of the present invention.
Figure 3:
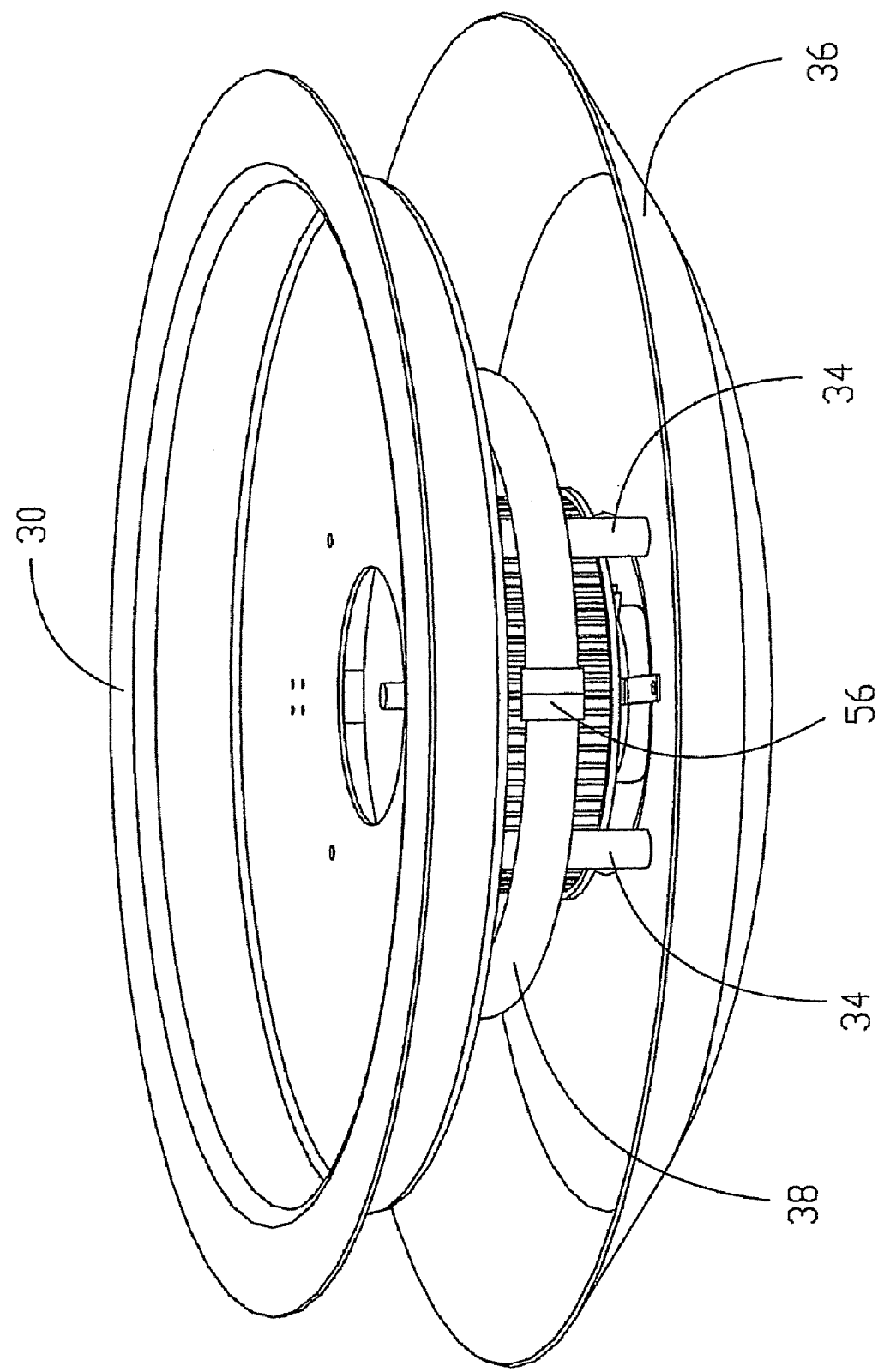
FIG. 3 is a pictorial view of the housing, UV-C source and baffle of the embodiment of FIG. 2 showing the general relationship of the fixture.

With reference to FIGS. 2 and 3, one embodiment of the fixture of the present invention includes a housing 30 adapted to be secured to the ceiling by any suitable conventional means such as the illustrated threaded fasteners 32. The housing 30 may take the form of a flat decorative cover for the ceiling aperture through which power is supplied to the fixture, but desirably has sufficient depth to enclose the controls 52 and hides a ceiling aperture. The housing 30 may be dependant from the ceiling but some portion thereof may extend upwardly into the plenum where it is desirable to reduce the extent to which the fixture extends downwardly into the room.

Dependant from the housing by a number of posts or stand-offs 34 is a baffle 36. Dependant from the baffle 36 is the air intake 50 and an optional source of visible light 40 for providing room illumination. Supported by the baffle 36 is an electric motor 42 the shaft 46 of which is upwardly connected to an impeller 48. Also supported by the baffle 36 intermediate the housing 30 and the baffle 36 is the source of UV-C radiation 38. In the preferred embodiment, the baffle, the electric motor with attached impeller, UV-C source, air intake and illumination source form a single assembly that is suspended from the housing by a plurality of posts or rods 34.

In operation, air from the room is drawn upwardly through a flaring air intake 50 by rotation of the impeller 48 to be exhausted laterally between the housing 30 and the baffle 36 over 360 degrees. The exhausted air passes through the UV-C radiation where it is treated, the treated air is mixed with the untreated air in the room by the mixed air is re-circulated to the intake 50, and the process is repeated.

The motor 42 is desirably located within the air intake 50 so that the motor 42 is cooled by the passing air. However, in another embodiment (not shown), the motor 42 is located above the impeller in the housing where impedance of air flow through the intake 50 is avoided but where the motor is deprived of the benefit of air cooling. In this later embodiment, the motor 42 and the controls 52 may extend upwardly into the aperture in the ceiling or plenum.

The room illumination source 40 may be any suitable convention source but is desirably a pair of circular, energy efficient, fluorescent bulbs supported by suitable conventional holders 54 the ends of which are vertically plugged into a mating female receptacle (connected to the ballast) via a four-pin. plug located on the bulb wall. The visible source may be housed in any suitable conventional glare reducing structure (not shown). The location of the source 40 of visible light laterally of the intake 50 avoids interference with the flow if air into the fixture, increasing the volume and reducing noise.

The UV-C source 38 may be any suitable conventional source such as germicidal fluorescent, light emitting diodes (LED's), mercury vapor and metal halide, but desirably is a pair of semi-circular germicidal fluorescent bulbs with end connectors that plug into a pair of diametrically opposed sockets 56. The bulbs of the source 38 are accessible in the space between the housing 30 and the baffle 36 and may be replaced as necessary without disassembly of the fixture.

In the preferred embodiment illustrated, the UV-C source 38 is desirably located just above the top of the baffle so that horizontal emissions are unimpeded as shown by the ray 58. While there may be some direct radiation from the top of the source that is below the horizontal, the angle below the horizon is sufficiently small that the radiation may not reach eye level within the room, and if reached, will be sufficiently diminished by the distance traveled to be inconsequential. Thus there is essentially no direct radiation from the fixture below the horizontal. To avoid exceeding the radiation threshold in the lower part of the room, the UV-C source can be lowered within the baffle, or the edges of the baffle raised slightly.

The housing 30 serves to limit the angle of emission as shown by ray 60 and thus the angle at which direct UV-C radiation on the ceiling may be reflected into the room. The upward angle is less than 45 degrees above the horizontal to prevent excessive reflection of direct radiation from the ceiling, and desirably is less than 35 degrees.

The housing 30 and baffle 36 thus define the direct UV-C radiation field and the spacing between them results in a field that is vertically broader than conventional beam fixtures and may be less intense since the air exiting the fixture remains longer in the radiation field. The use of a broader, less intense beam is several orders of magnitude more efficient (UV-C output per watt) than densely louvered beam fixtures.

Since the strength of the radiation is inversely related to the distance the radiation travels, limiting the angle of reflectance is beneficial in avoiding excessive radiation in the lower part of the room, e.g., generally considered to be the NIOSH recommended threshold between about 0.2 and 0.4 $\mu J/cm^2$ at "eye level", i.e., at a distance of about 60" from the floor.

Baffles such as louvers, or egg crate diffusers, may also be used within the air intake 50 to the extent UV-C radiation exiting the air intake 50 is excessive. In addition, the surfaces of the housing 30 and baffle 36 may be coated with an UV-C absorbing material to inhibit reflection, e.g., paints containing titanium dioxide.

Small ⅛" D red glass windows in the baffle 36 may be provided and will glow when the UV-C source is energized, This permits the operational status of the UV-C source to be determined from eye level and notice that the UV-C bulbs need changing.

The spacing between the housing 30 and the baffle 36 may be adjusted by the substitution of rods 34 having a differing length. The lowering of the baffle 36 by the use of longer rods 34 does not change the relative position of the UV-C source 38 and baffle 36. However, it does change the relative position of the UV-C source 38 and the housing 30, i.e., it opens the UV-C baffle aperture and thus changes the angle at which direct radiation from the source 38 may strike the ceiling and be reflected into the lower part of the room. However, if the fixture is used with higher ceilings, the intensity of the radiation may diminish sufficiently as the radiation travels from the source to the ceiling and back to the lower part of the room so as to avoid exceeding the radiation threshold.

The UV-C source 38 may be any suitable conventional source such as germicidal fluorescent, light emitting diodes (LED's), mercury vapor and metal halide. Desirably, the UV-C source 38 is a pair of semi-circular germicidal fluorescent bulbs with end connectors that plug into a pair of diametrically opposed sockets 56. The bulbs of the source 38 are accessible in the space between the housing 30 and the baffle 36 and may be replaced as necessary without disassembly of the fixture.

The impeller 48 is driven by the shaft 46 and desirably is substantially coextensive vertically with the spacing between the housing 30 and the baffle 36 to maximize lateral air flow past the UV-C source 38. The blades of the impeller 48 may be made of, or coated with, a material reflective of 50% or more of the inwardly radiated incident UV-C radiation further improving the efficiency of the fixture.

As earlier indicated, the controls 52 for the fixture are desirably carried within the housing 30. However, they may be carried by the baffle 36. The control of the operation of the fixture from within the room may be by hard wired switches or by a conventional remote control system. The specific electronic circuits within the controls 52 play no part in the present invention and may be any combination of suitable state-of-the-art controls. Desirably included within the control module is a receiver for remote control and a number of circuits for controlling the operation of the fixture, i.e., a three-speed switch or rheostat for motor control, an on-off switch and dimmer control for the visible light, and an on-off switch for the UV-C source. Optionally, a suitable conventional motion and/or noise detector may be included to automatically ratchet up the UV-C radiation to a level that exceeds the target threshold when there are no people in the room.

The controls 52 also include a manually settable ballast for the UV-C source, so that the intensity of the UV-C source may be set to avoid exceeding the target threshold in the lower part of the room under the specific conditions of the room, e.g., ceiling height, ceiling surface and reflectance, wall surfaces and furnishings, spacing of the Exposure to UV-C radiation has an adverse effect on many materials such as insulation for wiring and it is thus desirable to coat surfaces exposed to UV-C radiation with a UV-C resistant material such as aluminum foil or a synthetic equivalent such as polytetrafluoroethylene (PTFE) marketed as TEFLON®.

Among the advantages of the present invention are a practical size, e.g., about twelve inches vertically, that permits the use of the fixture with common ceiling heights. Additionally, the amount of energy consumed in creating an effective UV-C radiation field is greatly reduced. The shape of the radiation field may be controlled by a single mechanical adjustment and the intensity of the radiation field readily adjusted for specific installations. The UV-C source is readily accessible for replacement as is the visual light source.

While the foregoing is a description of preferred embodiments, many variations and modifications will naturally occur to those of skill in this art from a perusal hereof. The invention is therefore not to be limited to the embodiments disclosed, but defined only by the claims when accorded a full range of equivalents.

What is claimed is:

1. An in-room air sterilizer for a room having a planar ceiling not less than about eight feet from the floor, said sterilizer being suspended from the planar ceiling and adapted for connection through the planar ceiling to a source of electrical energy, said air sterilizer comprising:
   a housing that has a lateral dimension small relative to said room and that is spaced from the walls thereof;
   a UV-C radiation baffle located vertically below said housing and having a top surface;
   a source of UV-C radiation located between said housing and said baffle such that a bottom surface of said source is flush with a horizontal plane formed by said top surface of the baffle, wherein said source creates a radiation field extending laterally into the room around said housing, and wherein horizontal radiation emissions from said source are unimpeded by said baffle; and
   an air mover including an impeller generally at the same vertical level as said source and an electric motor driving said impeller, said air mover drawing air upwardly into said impeller and discharging air generally horizontally from said impeller into the radiation field,
   wherein the location of said source and said housing defines the upper limit of the angle of direct radiation from said source into the room and thus the maximum angle at which direct radiation is reflected from the planar ceiling into the room, said angle of direct radiation being not greater than about 35 degrees,
   wherein the location of said source and said baffle defines the lower limit of the angle of direct radiation into the field, said angle of direct radiation being not less than about zero degrees, and
   wherein the intensity of the radiation field inclusive of direct and reflected radiation is less than about 0.3 $\mu j/cm^2$ within about five feet of the room floor.

2. The sterilizer of claim 1 including a control circuit within said housing.

3. The sterilizer of claim 2 wherein said control circuit includes a receiver by which the operation of the fixture may be remotely controlled.

4. The sterilizer of claim 2 wherein said control circuit includes a motion detector to increase the intensity of the UV-C radiation when there are no people in the lower part of the room.

5. The sterilizer of claim 1 wherein the vertical distance between said housing and said baffle is about 3 inches.

6. The sterilizer of claim 1 wherein the vertical distance between said housing and said baffle is adjustable.

7. The sterilizer of claim 1 wherein total fixture depth is less than about 15 inches.

8. The sterilizer of claim 7 wherein total fixture depth is less than about 12 inches.

9. The sterilizer of claim 1 including a visible light source below said baffle.

10. The sterilizer of claim 9 wherein said visible light source is a circular fluorescent bulb.

11. The sterilizer of claim 10 including a glare reducing cover for said visible light source.

12. The sterilizer of claim 11 wherein said UV-C and said visible light sources are substantially vertically aligned.

13. The sterilizer of claim 1 wherein said UV-C source is a pair of semi-circular bulbs.

14. The sterilizer of claim 1 wherein said UV-C sources are accessible without removing said baffle from the fixture.

15. The sterilizer of claim 1 wherein said impeller is reflective of at least 50% of the UV-C radiation incident thereon from said UV-C source.

16. The sterilizer of claim 1 wherein said visible light source is above the lowest part of said air intake.

17. The sterilizer of claim 1 wherein said visible light source is not in the air intake path of said impeller.

18. The sterilizer of claim 1 including a filter for said UV-C source to reduce visible light.

19. The sterilizer of claim 1 wherein the upper surface of said baffle is UV-C absorptive.

20. The sterilizer of claim 1 wherein the outer surface of said housing is UV-C absorptive.

21. An in-room sterilizer for a room having a planar ceiling not less than about eight feet from the floor, said sterilizer being suspended from the ceiling and adapted for connection through the ceiling to a source of electrical energy, said air sterilizer comprising:
- a housing having a lateral dimension that is small relative to the room in which it is suspended and spaced from the walls thereof;
- a UV-C radiation baffle below said housing a distance not greater than about six inches;
- a source of UV-C radiation located between said housing and said baffle such that a bottom surface of said source is flush with a horizontal plane formed by said top surface of the baffle, wherein said source creates a radiation field extending laterally into the room around said housing, and wherein horizontal radiation emissions from said source are unimpeded by said baffle; and
- an air mover including an impeller generally at the same vertical level as said source and an electric motor driving said impeller, said air mover drawing air upwardly into said impeller and discharging air generally horizontally from said impeller into the radiation field,
- the total depth of said sterilizer being less than about 15 inches.

22. A ceiling fixture for sterilizing air within a room having a lower portion below about five feet, said fixture being laterally small relative to the room and spaced from the walls thereof, comprising:
- a UV-C radiation baffle having a top surface and located vertically below said fixture;
- a source providing a UV-C radiation field in the room external of the fixture, with the field;
  - (a) including essentially no direct radiation in the lower portion of the room;
  - (b) including essentially no ceiling reflected radiation in the lower portion of the room where the angle of reflection from the ceiling is less than about 15 degrees,
  - (c) the intensity of UV-C radiation in the lower portion of the room not exceeding about 0.3 $\mu J/cm^2$, and
  - (d) emitting horizontal radiation emissions from the source, unimpeded by the fixture; and
- an air mover for moving air through the UV-C field in a generally horizontal direction to effect mixing of room air and re-circulation of mixed room air through the fixture,
- wherein a bottom surface of the source is flush with a horizontal plane formed by the top surface of the baffle.

* * * * *

UNITED STATES PATENT AND TRADEMARK OFFICE
Certificate

Patent No. 7,763,212 B2                                                                                      Patented: July 27, 2010

On petition requesting issuance of a certificate for correction of inventorship pursuant to 35 U.S.C. 256, it has been found that the above identified patent, through error and without any deceptive intent, improperly sets forth the inventorship.
    Accordingly, it is hereby certified that the correct inventorship of this patent is: Melvin W. First, Newton, MA (US); Richard L. Vincent, Bloomfield, NJ (US); Philip W. Brickner, Bronx, NY (US); John J. McEllen, Chagrin Falls, OH (US)

Signed and Sealed this Fifth Day of April 2011.

*Jill A. Warden*
*Supervisory Patent Examiner*
*Art Unit 1773*
*Technology Center 1700*

UNITED STATES PATENT AND TRADEMARK OFFICE
CERTIFICATE OF CORRECTION

Page 1 of 1

PATENT NO. : 7,763,212 B2
APPLICATION NO. : 12/512647
DATED : July 27, 2010
INVENTOR(S) : John J. McEllen It is certified that error appears in the above-identified patent and that said Letters Patent is hereby corrected as shown below:

In column 1, line 21, replace "W-C" with --UV-C--;
In column 1, line 23, replace "W-C" with --UV-C--;
In column 1, line 26, replace "W-C" with --UV-C--;
In column 1, line 28, replace "W-C" with --UV-C--;
In column 1, line 29, replace "W-C" with --UV-C--;
In column 1, line 30, replace "W-C" with --UV-C--;
In column 1, line 37, replace "W-C" with --UV-C--; and
In column 1, line 39, replace "W-C" with --UV-C--.

Signed and Sealed this
Third Day of May, 2011

David J. Kappos
*Director of the United States Patent and Trademark Office*